United States Patent [19]
Gross et al.

[11] Patent Number: 5,586,067
[45] Date of Patent: Dec. 17, 1996

[54] SUPPORT ENHANCING DEVICE AND ASSOCIATED METHOD

[75] Inventors: Clifford M. Gross, Roslyn Harbor; Lin Bo, Wheatley Heights; Honzheng Lu, Deer Park, all of N.Y.

[73] Assignee: BCAM International, Inc., Melville, N.Y.

[21] Appl. No.: 277,230

[22] Filed: Jul. 19, 1994

[51] Int. Cl.$^6$ ............................ G01R 23/16; G06G 5/00; A43B 7/14; A47C 7/14
[52] U.S. Cl. .................. 364/576; 364/506; 364/509; 364/558; 324/76.21; 297/284.1; 36/88
[58] Field of Search ........................... 364/558, 559, 364/576, 508, 509, 505, 506; 324/76.29, 76.21; 297/284.1; 73/12.01, 12.08, 760, 172, 756; 36/136, 132, 93, 88, 71

[56] References Cited

U.S. PATENT DOCUMENTS

| | | |
|---|---|---|
| 5,060,174 | 10/1991 | Gross . |
| 5,170,364 | 12/1992 | Gross et al. . |
| 5,176,424 | 1/1993 | Tobita et al. ............... 297/284.1 |
| 5,230,249 | 7/1993 | Sasaki et al. .................. 73/714 |
| 5,283,735 | 2/1994 | Gross et al. . |

Primary Examiner—Emanuel T. Voeltz
Assistant Examiner—Hien Vo
Attorney, Agent, or Firm—Snell & Wilmer L.L.P.

[57] ABSTRACT

A device for supporting a human being comprises a superstructure defining a support surface in contact with a body part of a person and measurement componentry on the superstructure for periodically measuring a predetermined biomechanical parameter of the person's body part to determine a load distribution on the body part. The measurement componentry includes a fluid filled reservoir at the support surface and a pressure detector in operative engagement with fluid in the reservoir for monitoring changes in the pressure of the fluid, due, for example, to varying loads caused by physical activity. Circuitry is operatively coupled to the pressure detector for monitoring and characterizing changes in pressure of the fluid over time. Form control componentry is disposed on the superstructure and is operatively connected to the measurement componentry for automatically subjecting the support surface, in response to the determined load distribution, to forces tending to modify a contour of the support surface. The form control circuitry may include a pressurization source for modifying a base pressure of the reservoir fluid.

29 Claims, 4 Drawing Sheets

SUPPORT ENHANCING DEVICE AND ASSOCIATED METHOD

BACKGROUND OF THE INVENTION

This invention relates to a device and an associated method for improving the efficacy of a personal support. More particularly, this invention relates to a device and an associated method for automatically affecting the form, contour and/or support pressure of a personal support such as an article of clothing, a safety or protective device, or an article of furniture. This invention also relates to a method and associated apparatus for monitoring physical activity of a person to determine body comfort.

A recent ergonomic development in the field of clothing involves an athletic shoe which is provided with a manually actuatable pump for modifying the pressure of a support chamber in the shoe. The pump enables a user to adapt the shoe to the particular circumstances of use, increasing pressure in the chamber and thereby stiffening one or more panels or sides of the shoe for enhancing support or, alternatively, decreasing pressure to provide greater flexibility and augmented shock absorption.

Where the type and intensity of the athletic activity remains constant or uniform during an entire event, such as in a race, then the shoe pump design works acceptably well. However, where the kind and level of activity changes during an athletic event, the preselected pressure may become suboptimal. For example, during a tennis match, the user may change his or her tactics from consistent base line volleying to a frequent rush to the net. In a volleyball tournament, the role of a particular player may change from that of a setter to a hitter. The differences between the two tactics result in different kinds of stresses exerted on the foot. These stresses or loads differ from one another in impact frequency and intensity. The problem, of course, is that the wearer does not have an opportunity to modify the pressure in the pressurizable chamber in the middle of such athletic activity.

Similar considerations apply to other kinds of personal supports such as therapeutic braces and athletic equipment. For example, where a person is provided with a brace for supporting a strained muscle or ligament, certain kinds of stress or physical activity are desirable exercise, requiring reduced support in order to give the muscles an opportunity to exert themselves, while other kinds of stress are possibly dangerous to therapeutic mending, requiring greater support for protection. Once again, the problem is that the brace wearer or the individual's physical therapist is frequently unable to predict the kind and level of stress in advance of a physical activity to permit optimal adjustment of the brace, e.g., of pressurizable bladders in the brace.

Another kind of personal support surface is a bed or a chair. It would be desirable, for instance, to modify the support characteristics of a bed in accordance with the stress or loads experienced by different parts of the user's body, in order to minimize unhealthy stress distributions. Stress on a sleeper's body can be estimated in part by determining the posture of the sleeper. More specifically, a person sleeping on his stomach is apt to require different support than a person lying on his side or his back. Optimally, the rigidity or firmness of different parts of a mattress should be varied depending on the posture of the sleeper.

OBJECTS OF THE INVENTION

An object of the present invention is to provide a method for studying physical effects of an activity on a human body.

Another object of the present invention is to provide such a method which can be used in optimizing comfort, fit and/or load distribution of surfaces in contact with the human body.

Another, more particular, object of the present invention is to provide such a method which enables adaptation of comfort, fit and/or load distribution of such surfaces in accordance with changing load distributions or stresses of physcial activity.

A further object of the present invention is to provide a device which automatically implements the method of the invention.

These and other objects of the present invention will be apparent from the drawings and detailed descriptions herein.

SUMMARY OF THE INVENTION

A device for supporting a human being comprises, in accordance with the present invention, a superstructure defining a support surface in contact with a body part of a person, measurement componentry on the superstructure for periodically measuring a predetermined biomechanical parameter of the person's body part to determine a load distribution on the body part, and form control componentry disposed on the superstructure and operatively connected to the measurement componentry for automatically subjecting the support surface, in response to the determined load distribution, to forces tending to modify a contour of the support surface.

In some cases, form control componentry actually modifies a contour of the support surface. For example, where the support surface is on a bed, the surface conforms to the profile of the user in contact with the bed. When a user turns to lie on his or her back, the bed changes contour to insert a hump into the hollow of the lower back and to slightly prop up the head. If the user changes to a stomach-down position, the form control componentry modifies the contour of the bed surface to slightly reduce the elevation of the head and to receive a protruding belly or lower abdomen, thereby relieving possible stress on the lower back.

In other cases, the contour of the support surface does not appreciably change, owing to continued contact of the same body part of the individual user. However, differing amounts of force or pressure are applied to the support surface, and therefore to the user, to compensate for changes in load or stress on the particular body part. Where the support surface is a shoe panel, whether a sole, a side panel or an upper, differing amounts of pressure are applied to the wearer's foot, to compensate for changes in frequency and intensity of impacts, as described in detail hereinafter.

The measurement componentry may include a fluid filled reservoir at the support surface and a pressure detector in operative engagement with fluid in the reservoir for monitoring changes in the pressure of the fluid, due, for example, to varying loads caused by physical activity. In the case of a shoe, a therapeutic brace, or a piece of protective athletic padding, the changing physical activity of the user results in different load distributions over time. Accordingly, in such applications, the measurement componentry further includes circuitry operatively coupled to the pressure detector for monitoring and characterizing changes in pressure of the fluid over time.

According to another feature of the present invention, the circuitry for monitoring and characterizing changes in pressure of the fluid over time includes a first subcircuit for determining measured pressure as a function of time, a second subcircuit operatively connected to the first subcircuit for determining differential pressures and computing a Fourier Transform on the pressure function determined by the first subcircuit, a third subcircuit for storing a table of optimal comfort pressures as a function of frequency and differential pressure, and a fourth subcircuit operatively connected to the second subcircuit and the third subcircuit for selecting, from the table, a comfort pressure based at least in part on a frequency and differential pressure computed by the second subcircuit.

Generally, the comfort pressures stored in the third subcircuit are determined experimentally. A series of test subjects are subjected to each of a plurality of different load distributions over time and to a plurality of different test pressures at the respective support surface for each load distribution. The subjects are asked to select which test pressure is most comfortable. A statistical mean, median or mode is computed from the selected test pressures. That mean, median or mode is designated the comfort pressure for the respective load distribution.

Accordingly, whenever the measurement componentry detects that a particular load distribution is in effect, the form control componentry operates to subject the support surface to the comfort pressure which was previously determined experimentally as being optimal for the detected load distribution. Generally, it is expected that, to simplify processing and to decrease the amount of memory required, load distributions will be classed into categories. Each category will cover a range of load distributions, but will correspond to one comfort pressure.

According to another feature of the present invention, the form control componentry includes means operatively connected to the reservoir for modifying the pressure exerted by the fluid on the user's body part. Thus, the same medium used to detect loading may be used for optimizing comfort, fit and/or or support of the support surface.

As mentioned above, the measurement componentry may function to monitor frequency and intensity of impacts on the body part. This operation is particularly advantageous or purposeful where the support superstructure is a protective athletic device such as a shoe, a knee brace, or a shoulder pad. The effect of therapeutic braces is also improved or optimized where measurement componentry is provided for monitoring frequency and intensity of impacts on the braced body part. For example, the degree of pressure applied to a knee or leg brace, and thus the tightness of the fit of the brace to the knee or leg, can be reduced where the individual is resting or walking slowly, to permit slow strengthening of the leg muscles. In contrast, when the individual is running or jumping, the degree of pressure applied to a knee or leg brace, and thus the tightness of the fit of the brace to the knee or leg, can be increased to provide greater support. It is also possible to program the form control componentry so that the degree of support provided varies over time. As healing progresses, less support is applied even in stressful activities such as running or jumping.

It is to be understood, therefore, that the measurement componentry is adapted to detecting different types of motion of the body part. This is possbile because the measurement componentry analyzes biomechanical loads as functions of time. Fast Fourier Transforms or other mathematical techniques may be used to characterize or categorize types of motion. A simple technique would be to monitor relative load peaks and to classify load distributions according to the number of peaks of different magnitudes within an arbitrary time period.

A related method for supporting a human being comprises, in accordance with the present invention, the steps of (a) providing a superstructure defining a support surface, (b) placing a body part of a person in contact with the support surface, (c) upon engagement of the body part with the support surface, periodically and automatically measuring a predetermined biomechanical parameter of the person's body part to determine a load distribution on the body part, and (d) automatically subjecting the support surface, in response to the determined load distribution, to forces tending to modify a contour of the support surface.

Where a fluid filled reservoir is provided at the support surface and is coupled with the superstructure, the step of measuring includes the step of detecting pressure of the fluid in the reservoir. As noted above, the step of measuring may further include the step of monitoring and characterizing changes in pressure of the fluid over time. More particularly, the characterization of a load distribution over time may be implemented by the steps of (i) automatically determining measured pressure as a function of time, (ii) automatically computing a Fourier Transform on the determined pressure function and determining differential pressures, (iii) storing a table of optimal comfort pressures as a function of frequency and differential pressure, and (iv) automatically selecting, from the table, a comfort pressure based at least in part on a frequency and differential pressure computed during the step of computing. This technique is especially effective to monitor frequency and intensity of impacts on the body part or, alternatively viewed, to monitor types of motion of the body part.

Pursuant to a further feature of the present invention, the step of subjecting the support surface, in response to the determined load distribution, to forces tending to modify a contour of the support surface includes the step of modifying the pressure of the fluid, thereby altering pressure exerted by the support surface on the body part.

The support surface may be a chair back and the step of measuring includes the step of monitoring biomechanical stress on the person's back.

A shoe comprises, in accordance with a particular embodiment of the present invention, a superstructure defining a support surface positionable in contact with a person's foot, measurement componentry on the superstructure for periodically measuring frequency and magnitude of impacts on the person's foot, and form control componentry disposed on the superstructure and operatively connected to the measurement componentry for automatically subjecting the support surface, in response to the measured frequencies and magnitudes of impacts, to forces tending to modify a contour of the support surface to optimize omfort, fit, and/or load distribution.

In accordance with a further feature of this particular embodiment of the invention, the measurement componentry of the shoe includes a fluid filled reservoir at the support surface and a pressure detector in operative engagement with fluid in the reservoir.

In accordance with a further feature of this particular embodiment of the invention, the measurement componentry of the shoe further includes means operatively coupled to the pressure detector for monitoring and characterizing changes in pressure of the fluid over time. As discussed above with respect to a more general conceptualization of the present invention, the monitoring and characterizing means includes a first subcircuit for determining measured pressure as a function of time, a second subcircuit operatively connected to the first subcircuit for determining differential pressures and computing a Fourier Transform on the pressure function determined by the first subcircuit, a third subcircuit for storing a table of optimal comfort pressures as a function of frequency and differential pressure, and a fourth subcircuit operatively connected to the second subcircuit and the third subcircuit for selecting, from the table, a comfort pressure based at least in part on a frequency and differential pressure computed by the second subcircuit. As additionally discussed hereinabove with reference to the more general concenptualization of the invention, the form control componentry includes means operatively connected to the reservoir for modifying the pressure of the fluid.

The support surface may be the sole, a side panel or of a shoe. In the case of a high topped shoe, the support panel may surround the ankle. It is to be noted that a shoe in accordance with the present invention may be provided with a plurality of pressurizable chambers. A single pressure detector may be connected to all of the chambers for sequentially sampling (in a multiplexing process) pressures of the different chambers to determine load distributions for each of the chambers separately. Alternatively, the pressure detector may be operative to sample sequential pressures from only one chamber, that chamber being used as the standard by which the comfort pressures of the other chambers are set. It is to be noted that, for a shoe or other similar pressurizable support, the "comfort pressure" becomes a minimum or base pressure relative to which changes pressure of or differential pressures are indicative of load or stress on the foot or other body part which is in contact with the support.

A method for studying physical effects of an activity on a human body comprises, in accordance with a more general conceptualization of the present invention, the steps of (1) providing a superstructure defining a support surface, (2) placing a body part of a person in contact with the support surface, (3) providing a stress detector on the superstructure so that the detector can measure physical stress in the body part, (4) operating the detector, upon engagement of the body part with the support surface, to periodically and automatically measure physical stress of the body part, and (5) automatically analyzing physical stress measured during the step of operating to obtain a biomechanical distribution of the measured stress.

Pursuant to a further feature of the present invention, the step of analyzing includes the step of automatically characterizing the measured stress as a function of time and more specifically includes the step of automatically computing a Fourier Transform on the measured stress as a function of time. Additionally or alternatively, the step of analyzing includes the step of identifying the measured stress as falling within one of a plurality of predefined classes of stressing activity.

Where a fluid filled reservoir is provided at the support surface and is coupled with the superstructure, the detector being in operative contact with the fluid, and the step of operating the detector detect pressure of the fluid in the reservoir.

A method in accordance with the present invention facilitates the study of physical effects of an activity on a human body and particularly on a part of the body such as the foot, the back, the torso, the knee, the shoulder, etc. In these cases, the supporting superstructure may be a shoe, a chair, a bed, a knee brace, a shoulder pad, respectively. Moreover, the invention enables an automatic and essentially real time adjustment of the particular support in order to optimally conform the support to a changing load distribution, posture or form of the particular body part of the user. A method in accordance with the present invention serves to optimize comfort, fit and/or load distribution of surfaces in contact with the human body.

A device in accordance with the present invention automatically implements the method of the invention.

DETAILED DESCRIPTION

Figure 1:
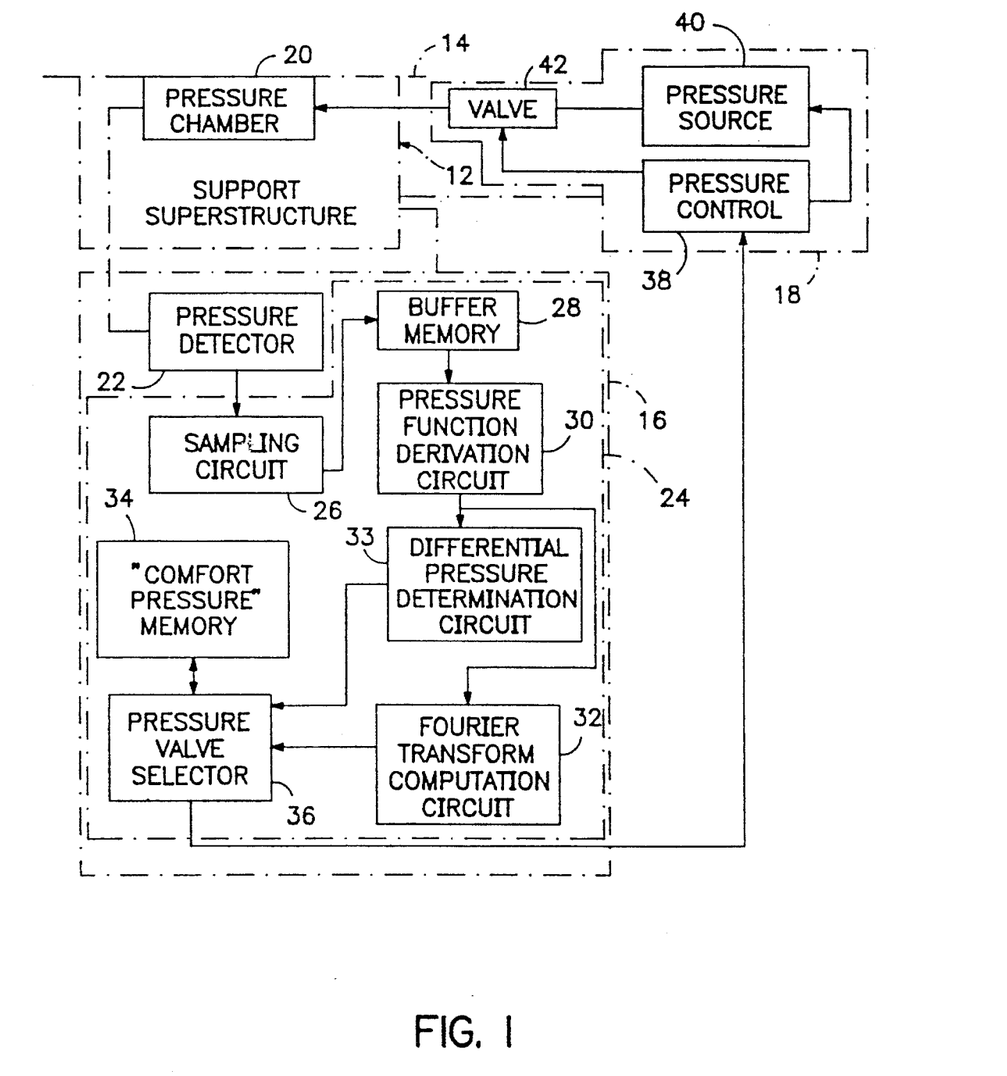
FIG. 1 is a block diagram of a support device for a human being, with automatic pressure or contour control in accordance with the present invention.

As illustrated in FIG. 1, a support device or system for a human being, with automatic pressure or contour control comprises a superstructure, frame, or housing 12 defining a support surface 14 positionable in contact with a body part of a person (not shown). Measurement componentry 16 is provided on superstructure 12 for periodically measuring a predetermined biomechanical parameter, e.g., physical stress, of the person's body part to determine a load distribution on the body part. Form control componentry 18 is disposed on superstructure 12 and is operatively connected to measurement componentry 16 for automatically subjecting support surface 14, in response to the determined load distribution, to forces tending to modify a contour or shape of support surface 14.

Figure 4:
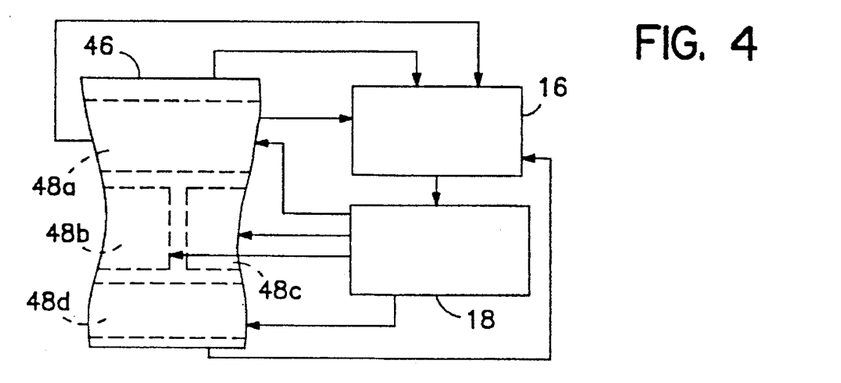
FIG. 4 is a diagram showing another particular embodiment of the device of FIG. 1.

Measurement componentry 16 includes or is connected to a fluid filled reservoir or chamber 20 which is at support surface 14. At least that portion of chamber 20 defined by or adjacent to support surface 14 is partially flexible to enable a modification of the contour or shape of support surface 14. Measurement componentry 16 further includes a pressure detector 22 in operative engagement with fluid in pressure chamber 20 for monitoring changes in the pressure of the fluid, due, for example, to varying loads caused by physical activity of the user or wearer of the support device. In the case of a shoe (FIG. 2), a therapeutic brace (FIG. 4), or a piece of protective athletic padding (not shown), the changing physical activity of the user results in different load distributions over time. To satisfactorily handle such applications, measurement componentry 16 includes pressure monitoring circuitry 24 operatively coupled to pressure detector 22 for characterizing changes in pressure of the fluid in pressure chamber 20 over time.

Pressure monitoring circuitry 24 includes a sampling circuit 26 operatively coupled to detector 22 for periodically sampling the fluid pressure in chamber 20, as sensed by detector 22. Sampling circuit 26 is electrically tied to a buffer memory 28 which stores a predetermined number of successive pressure values. Pressure monitoring circuitry 24 further includes a subcircuit 30 linked at an output to buffer memory 28 for deriving measured differential pressure as a function of time.

A second subcircuit 32 of pressure monitoring circuitry 24 operatively connected at an output to subcircuit 30 functions to compute a Fourier Transform on the pressure function determined by subcircuit 30, converting pressure function of time to a spectral (frequency) function. Subcircuit 32 functions in conjunction with another subcircuit 33 of pressure monitoring circuitry 24 operatively tied at an output to subcircuit 30. Subcircuit 33 operates to determine differential pressures associated with spectral frequencies computed by subcircuit 32.

Another subcircuit 34 of pressure monitoring circuitry 24 is a memory which stores a table of optimal comfort pressures as a function of frequency and differential pressure. Subcircuit 34 is accessed by a pressure value selection subcircuit 36 which is operatively connected to Fourier computation subcircuit 32 and determination subcircuit 33 for receiving calculated frequency and pressure data therefrom. In response to that pressure and frequency data, subcircuit 36 selects a "comfort pressure" from the table of such values stored in memory 34.

The comfort pressures stored in memory subcircuit 34 represent optimal pressures for the fluid in chamber 20, i.e., pressures which maximize comfort and support for the wearer, depending on the type and intensity of physical activity and accordingly on the load distribution experienced by the body part in contact with support superstructure 12. Once determined by pressure monitoring circuitry 24, the optimal pressure (the comfort pressure selected from memory 34) is impelemented in pressure chamber 20 by form control componentry 18. Componentry 18 includes a pressure control circuit 38 connected at an output to pressure value selector subcircuit 36 and at an input to a pressure source or pressurization element 40 such as a pump. Pressure source 40 is connected to pressure chamber via a valve 42 which is responsive to pressure control 38. Valve 42, which is part of form control componentry 18, is controlled to release pressure fluid from chamber 20 or to admit more fluid into that chamber from pressure source 40, in accordance with control signals from pressure control 38.

The comfort pressures stored in memory subcircuit 34 are determined empirically. A series of test individuals are subjected to each of a plurality of different load distributions over time and to a plurality of different test pressures at the respective support surface for each load distribution. The subjects are asked to select which test pressure is most comfortable. A statistical mean, median or mode is computed from the selected test pressures. That mean, median or mode is designated the comfort pressure for the respective load distribution.

As an alternative technique to tabular comfort data storage and access, subcircuit 36 may compute a comfort pressure from the calculated frequency and pressure data from subcircuits 32 and 33 by utilizing a multiple regression equation whose coefficients are empirically determined and stored, e.g., in memory subcircuit 34. The exact values of the coefficients will vary depending on the number of test subjects and their responses.

Figure 7:
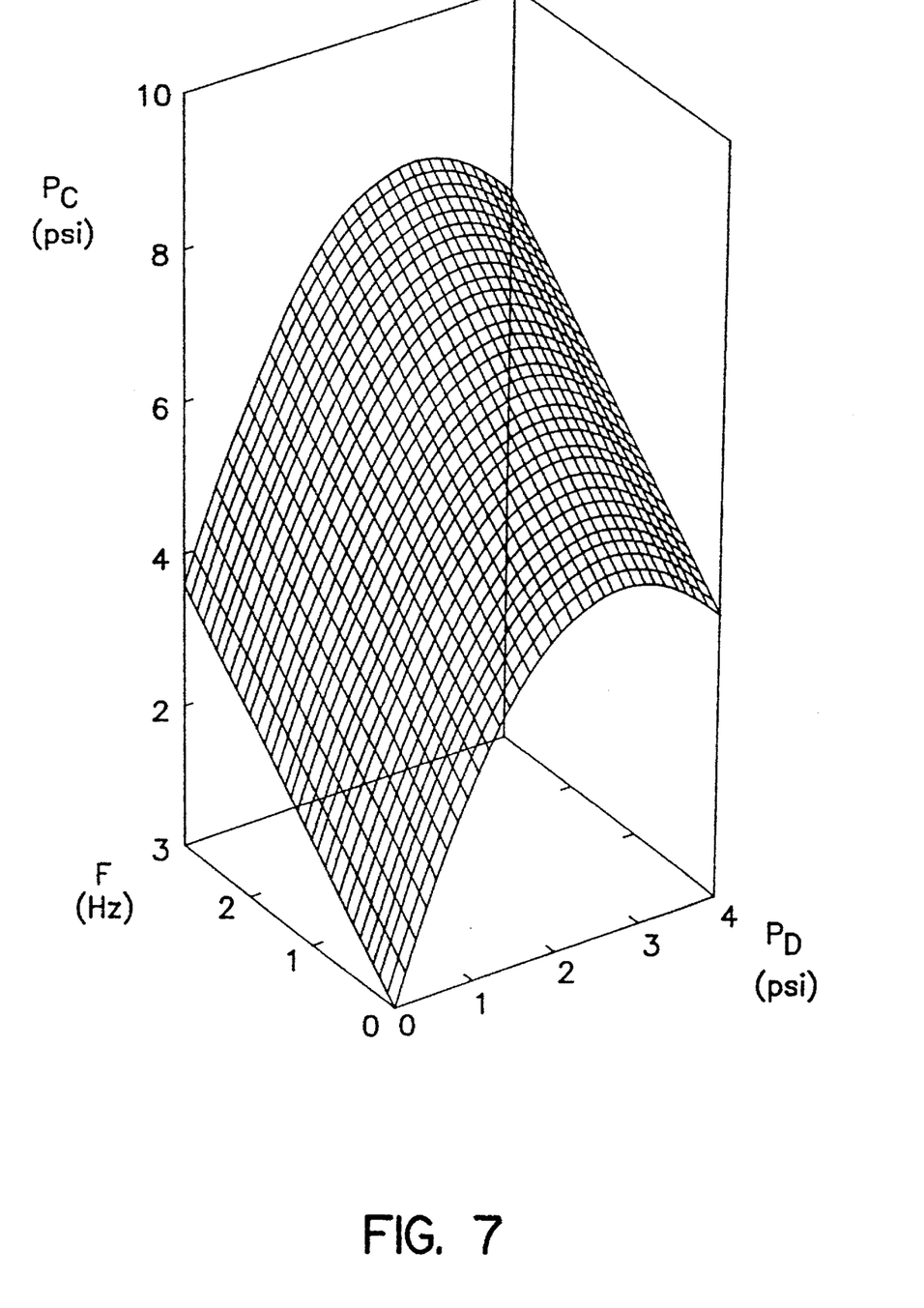
FIG. 7 is a graph showing comfort pressures of a bladder or pressure chamber in an athletic shoe as a function of frequency and differential pressure as computed via a Fourier Transform.

FIG. 7 is a graph showing comfort pressures $P_C$ of a bladder or pressure chamber in an athletic shoe as a function of frequency F and differential pressure $P_D$ as computed via a Fourier Transform. The graph of FIG. 7 is derived using the following multiple regression equation as a model:

$$P_C = -0.57 \times (P_D)^2 + 3.22 \times P_D + 1.18 \times F.$$

In the model significance test for this illustrative multiple regression equation, $p < 0.0001$, while $R^2 = 0.89$.

Figure 2:
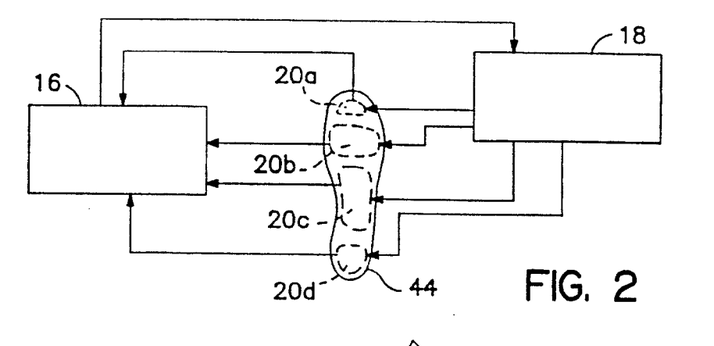
FIG. 2 is a diagram showing a particular embodiment of the device of FIG. 1.

FIG. 2 schematically depicts a particular embodiment of the device of FIG. 1 where superstructure 12 takes the form of an athletic shoe 44. Support surface 14 may in that case take the form of an insole (not shown) of shoe 44. Pressure chamber 20 is one of a plurality of pressure chambers 20a, 20b, 20c, 20d disposed under different areas of the sole, namely, the toe, the balls, the instep, and the heel, respectively. Pressure chambers 20a, 20b, 20c, 20d are operatively connected to sampling circuit 26 of measurement componentry 16 via one or more pressure detectors 22 (not shown) and pressure source 40 of form control componentry 18 via valve 42. In this case, sampling circuit 26 sequentially samples the pressures of the different chambers 20a, 20b, 20c, 20d, while subcircuit 30 determines four different functions of pressure vs. time. Subcircuit 32 performs a Fourier Transform computation for each of the pressure functions, while subcircuit 36 selects four comfort pressures based on the results of the Fourier Transform. In response to pressure control 38, valve 42 and pressure source 40 function to institute the selected comfort pressures in the respective chambers 20a, 20b, 20c, 20d of shoe 44.

In the case of shoe 44, measurement componentry 16 effectively determines the frequency and magnitude of impacts on the user's foot. In response to this determination, form control componentry 18 modifies the base pressures in chambers 20a, 20b, 20c, 20d to optimize comfort for the user. Thus, the pressures applied to the fluid in chambers 20a, 20b, 20c, 20d where the user jumps frequently as in basketball or volleyball will be different from the pressures applied to the fluid in chambers 20a, 20b, 20c, 20d where the user has a lesser, more constant impact on the foot as in field and track activities.

The method of operation of the device of FIG. 1 as applied to an athletic shoe will enable adaptation of the shoe pressure chambers 20a, 20b, 20c, 20d to different ranges of activity even during the same exercise or competition. Accordingly, during a tennis match, pressure monitoring circuitry 24 can detect a change in tactics from a consistent base line volleying to a frequent rush to the net and induce form control componentry 18 to modify the pressure in chambers 20a, 20b, 20c, 20d accordingly. This capability arises from the monitoring of pressure changes over time and the automatic analysis of those pressure changes to provide an optimal comfort pressure.

In the embodiment of FIG. 2, a single pressure detector 22 may be connected via valving (not shown) to the different pressure chambers 20a, 20b, 20c, 20d. Alternatively, multiple pressure detectors may be provided. In another alternative system, pressure detector 22 may be operative to sample sequential pressures from only one chamber 20a, 20b, 20c, or 20d which is then used as the standard by which the comfort pressures of the other chambers are set. It is to be noted that, for a shoe or other similar pressurizable support, the "comfort pressure" becomes a minimum or base pressure relative to which changes of ditterentail pressures are indicative of load or stress on the foot or other body part which is in contact with the support.

In alternative specific applications or embodiments, support surface 14 may be substantially the entire insole of an shoe, a side panel, an upper, or in the case of a high topped shoe, an ankle portion.

Figure 3:
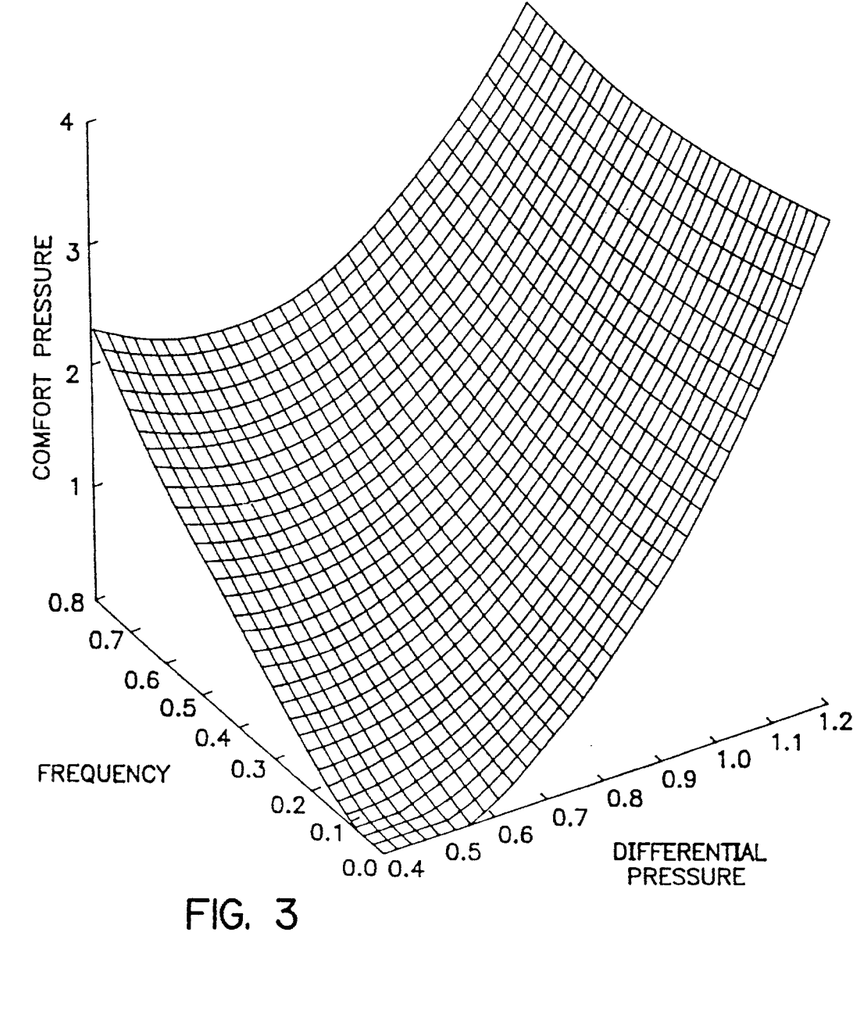
FIG. 3 is a graph showing comfort pressures of a pressurizable or conformable support surface in accordance with the present invention as a function of frequency and differential pressure as computed via a Fourier Transform.

FIG. 3 is a graph illustrating, by way of example, a mathematical comfort surface. With an arbitray scale, the z-axis represents an emirically determined comfort pressure as a function of an impact frequency and magnitude as determined via Fourier Transforms. The information represented by the graph of FIG. 3 is encoded in tabular form and stored in memory 34.

Where a Fourier Transform computation results in a plurality of frequency and magnitude points, selection subcircuit 36 may operate to select a comfort pressure based on a categorization of the results. Such categories may be predefined, for example, in accordance with the particular applications intended for the support. For an athletic shoe, relevant classifications may include (a) low impact, high frequency impacts, (b) high impact, low frequency, (c) high impact, high frequency, and (d) low impact, low frequency. Upon an analysis of transform results to determine the category, selector subcircuit 36 accesses memory 34 to determine optimal pressurization.

Where support superstructure 12 (FIG. 1) is a protective athletic device such as a shoe 44 (FIG. 2), a knee brace 46 (FIG. 4), or a shoulder pad (not shown), measurement componentry 16 advantageously functions to monitor frequency and intensity of impacts. The effect of therapeutic braces is also improved or optimized where measurement componentry 16 is provided for monitoring frequency and intensity of impacts on the braced body part. For example, the degree of pressure applied to knee or leg brace 46 (FIG. 4), and thus the tightness of the fit of the brace to the knee or leg, can be reduced where the individual is resting or walking slowly, to permit slow strengthening of the leg muscles. In contrast, when the individual is running or jumping, the degree of pressure applied to a knee or leg via pressure chambers 48a, 48b, 48c, 48d in brace 46, and thus the tightness of the fit of the brace to the knee or leg, can be increased to provide greater support. It is also possible to program form control componentry 18 so that the degree of support provided varies over time. As healing progresses, less support is applied even in stressful activities such as running or jumping.

Figure 5:
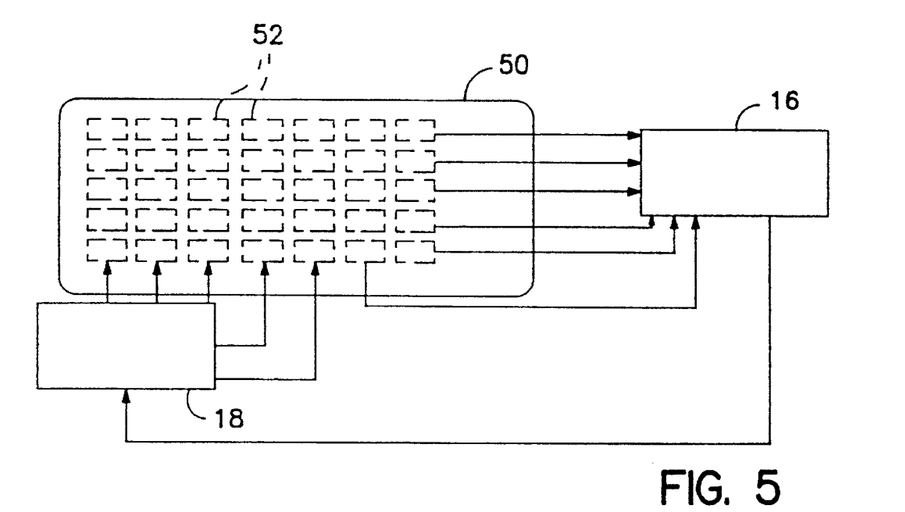
FIG. 5 is a diagram showing a further particular embodiment of the device of FIG. 1.

FIG. 5 depicts a bed 50 provided with a plurality of relatively small pressurizable chambers 52 disposed in a rectangular array. Chambers 52 are operatively connected to pressure sampling circuit 26 of measurement componentry 16 via one pressure detector or, alternatively, respective detectors and to pressure source 40 of form control componentry 18 via valving (not shown). In the case of bed 50, it is in many instances not so important to measure changes over time, but to determine whether a change in posture has occurred and to determine the new posture for purposes of modifying the pressurization of chambers 52 to maximize comfort.

During steady state operation of the system of FIG. 5, the inputs from pressure chambers 52 are monitored to detect any change in loading. Once a change in loading has occurred, the differential pressures are compared to pre-established load distributions which have been stored in an internal memory. This comparison results in a determination of the new loading, i.e., the new posture assumed by the person on the bed. Upon determining the new posture, a memory of comfort pressure distributions is consulted to ascertain a most comfortable pressure distribution, as determined empirically. Pressure source 40 and its associated valving is then actuated to implement the optimal load distribution.

In the case of bed 50, form control componentry 18 actually modifies a contour of support surface 14 of bed 50. Surface 14 conforms at least partially to the profile of the user in contact with the bed. When a user turns to lie on his or her back, the bed changes contour to insert a hump into the hollow of the lower back and to slightly prop up the head. If the user changes to a stomach-down position, form control componentry 18 modifies the contour of the bed surface to slightly reduce the elevation of the head and to receive a protruding belly or lower abdomen, thereby relieving possible stress on the lower back.

Figure 6:
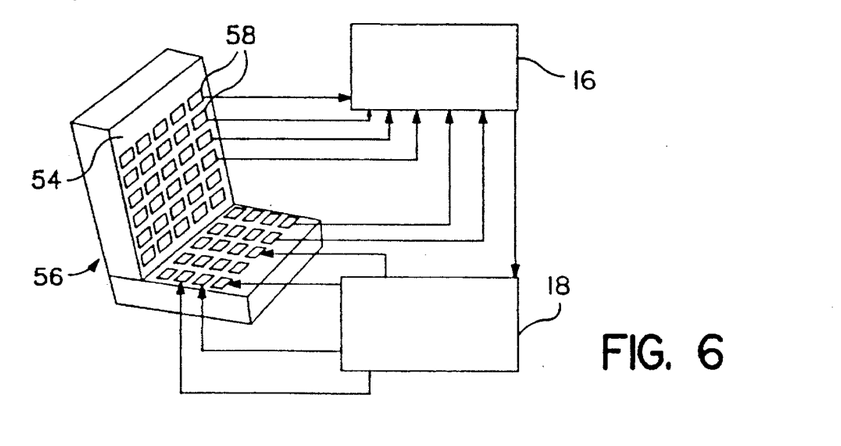
FIG. 6 is a diagram showing yet another particular embodiment of the device of FIG. 1.

FIG. 6 shows support surface 14 as a back 54 of a chair 56. In this case, pressure monitoring circuitry 24 of measurement componentry 16 monitors, in part, biomechanical stress on the user's back as sensed via pressure chambers 58.

In an alternative mode of operation of form control componentry 18 for a bed or chair, the base pressures of an array of pressure chambers are controlled to stimulate desirable motion of the user. In contrast to conventional mechanical beds where the user passively experiences a massage, a bed or chair may be controlled so as to induce desirable movement of the user. Thus, during a night's sleep, a person may be induced, through intelligent control componentry, to move through a prescribed series of positions empirically determined to optimize comfort, relaxation and sleep.

The techniques and devices described herein may be used to study the effects of a physical activity on a human body. Thus, measurement componentry 16, in periodically and automatically measuring physical stress of a body part in contact with support surface 14 and in automatically analyzing physical stress to obtain a distribution of the measured stress, provides useful information to biomechanical investigators researching the reactions of human tissue and organs to differing kinds and levels of physical loading.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that pressure or contour control at the contact surface may be implemented in at least some applications by means other than hydraulic or pneumatic. Multiple electric motors operating respective rack and pinion mechanisms may accomplish surface control.

In addition, other kinds of biomechanical parameters may be measured to determine loading of a body part. For instance, local galvanic skin response as an indicator of muscle exertion.

It is to be further noted that mathematical techniques other than the Fourier Transform may be used to characterize or categorize types of motion for purposes of optimizing comfort, fit, and load distribution of surfaces which come into contact with the body. For instance, after a digital filtering to remove spurious peaks, relative or local load peaks are detected by deriving and analyzing first and second derivatives of a pressure function as dervied by subcircuit 30. The load peaks are automatically correlated with the respective pressure magnitudes to determine load distributions. The load distributions are then classified according to the number of peaks of different magnitudes within an arbitrary time period. A load distribution thus measured can be matched with a pre-determined load category and thereby paired with a respective empirically determined comfort pressure.

Accordingly, it is to be understood that the drawings and descriptions herein are proffered by way of example to facilitate comprehension of the invention and should not be construed to limit the scope thereof.

What is claimed is:

1. A device for supporting a human being, comprising:
   a structure having a configurable contoured support surface;

a sensing device associated with said structure, said sensing device configured to measure an input parameter, reflective of a pressure distribution of a body part of a person;

a memory device for storing optimal comfort data and said pressure distributions determined by said sensing device;

a surface configuration device associated with said structure; and a processor associated with said sensing device, said memory and said surface configuration device, wherein said processor;

computes a differential pressure and frequency function using pressure distributions determined by said sensing device and stored in said memory device;

determines an optimal pressure distribution for the person's body part using the computed differential pressure and frequency function and the optimal comfort data stored in said memory device; and operates said surface configuration device so as to change a contour of said support surface so that the optimal pressure distribution is enacted on the person's body part.

2. The device defined in claim 1 wherein said sensing device includes a fluid filled reservoir at said support surface and a pressure detector in operative engagement with fluid in said reservoir.

3. The device defined in claim 2 wherein said surface configuration device includes means operatively connected to said reservoir for modifying the pressure of said fluid.

4. The device defined in claim 1, wherein said processor includes:

a first circuit configured for determining a measured pressure distribution as a function of time;

a second circuit operatively connected to said first circuit and configured for determining differential pressures and computing a Fourier Transform on the pressure function determined by said first circuit; and a third circuit operatively connected to said second circuit and said memory device, wherein said third circuit is configured for selecting, from the optimal comfort data stored in said memory device, a comfort pressure distribution based at least in part on a frequency and differential pressure computed by said second circuit.

5. The device defined in claim 1 wherein said surface configuration device includes a fluid filled reservoir at said support surface and means operatively connected to said reservoir for modifying the pressure of said fluid, thereby altering pressure exerted by said support surface on said body part.

6. The device defined in claim 1 wherein said sensing device and said processor include means for monitoring frequency and intensity of impacts on said body part.

7. The device defined in claim 1 wherein said sensing device and said processor include means for monitoring types of motion of said body part.

8. The device defined in claim 1 wherein said structure includes a panel of a shoe, said sensing device and said processor including means for monitoring frequency and intensity of impacts on a foot of the person.

9. The device defined in claim 1 wherein said support surface is a chair back and said sensing device and said processor include means for monitoring biomechanical stress on the person's back.

10. A method for supporting a human being, comprising the steps of:

providing a structure defining a configurable contoured support surface;

placing a body part of a person in contact with said support surface;

upon engagement of the body part with said support surface, periodically and automatically measuring an input parameter to determine a pressure on the body part;

automatically determining measured pressure as a function of time and frequency;

storing table of optimal comfort pressures;

automatically selecting, from the table, an optimal comfort pressure; and automatically subjecting said support surface, in response to the selected optimal comfort pressure, to forces tending to modify a contour of said support surface.

11. The method defined in claim 10 wherein a fluid filled reservoir is provided at said support surface and is coupled with said structure, said step of measuring including the step of detecting pressure of said fluid in said reservoir.

12. The method defined in claim 11 wherein said step of subjecting includes the step of modifying the pressure of said fluid.

13. The method defined in claim 10 wherein said step of automatically determining measured pressure includes the step of:

automatically computing a Fourier Transform on the determined pressure function and determining associated differential pressures.

14. The method defined in claim 10 wherein a fluid filled reservoir is provided at said support surface and is coupled with said structure, said step of subjecting including the step of modifying the pressure of said fluid, thereby altering pressure exerted by said support surface on said body part.

15. The method defined in claim 10 wherein said step of measuring includes the step of periodically and automatically monitoring frequency and intensity of impacts on said body part.

16. The method defined in claim 10 wherein said step of measuring includes the step of periodically and automatically monitoring types of motion of said body part.

17. The method defined in claim 10 wherein said structure includes a panel of a shoe, said step of measuring including the step of monitoring frequency and intensity of impacts on a foot of the person.

18. The method defined in claim 10 wherein said support surface is a chair back and said step of measuring includes the step of monitoring biomechanical stress on the person's back.

19. A shoe comprising:

a structure defining a configurable contoured support surface positionable in contact with a person's foot;

a sensing device associated with the structure for measuring frequency and magnitude of impacts on the person's foot;

a memory device for storing optimal comfort data and the frequency and magnitude of impacts determined by said sensing device;

a surface configuration device associated with said structure; and a processor associated with said sensing device, said memory device and said surface configuration device, wherein said processor;

computes a differential pressure and frequency function using the frequency and magnitude of impacts measured by said sensing device and stored in said memory device;

determines an optimal comfort, fit or pressure distribution for the person's foot using the computed differential pressure and frequency function and the optimal comfort data stored in said memory device; and operates said surface configuration device so as to change a contour of said support surface so that the optimal comfort, fit or pressure distribution is enacted on the person's foot.

20. The device defined in claim wherein said sensing device includes a fluid filled reservoir at said support surface and a pressure detector in operative engagement with fluid in said reservoir.

21. The device defined in claim 20 wherein said surface configuration device includes means operatively connected to said reservoir for modifying the pressure of said fluid.

22. The device defined in claim 19, wherein said processor includes:

a first circuit configured for determining a measured pressure distribution as a function of time;

a second circuit operatively connected to said first circuit and configured for determining differential pressures and computing a Fourier Transform on the pressure function determined by said first circuit; and a third circuit operatively connected to said second circuit and said memory, wherein said third circuit is configured for selecting, from the optimal comfort data stored in said memory, a comfort pressure distribution based at least in part on a frequency and differential pressure computed by said second circuit.

23. The device defined in claim 19 wherein said surface configuration device includes a fluid filled reservoir at said support surface and means operatively connected to said reservoir for modifying the pressure of said fluid, thereby altering pressure exerted by said support surface on the person's foot.

24. A method for studying physical effects of an activity on a human body, comprising the steps of:

providing a structure defining a support surface;

placing a body part of a person in contact with said support surface;

providing a stress detector on said structure so that said detector can measure physical stress in said body part;

upon engagement of said body part with said support surface, operating said detector to periodically and automatically measure physical stress of said body part; and automatically analyzing physical stress measured during said step of operating to obtain a biomechanical distribution of the measured stress.

25. The method defined in claim 24 wherein said step of analyzing includes the step of automatically characterizing the measured stress as a function of time.

26. The method defined in claim 25 wherein said step of characterizing includes the step of automatically computing a Fourier Transform on the measured stress as a function of time.

27. The method defined in claim 25 wherein said step of analyzing includes the step of identifying the measured stress as falling within one of a plurality of predefined classes of stressing activity.

28. The method defined in claim 24 wherein a fluid filled reservoir is provided at said support surface and is coupled with said structure, said detector being in operative contact with said fluid, and wherein the step of operating includes the step of detecting pressure of said fluid in said reservoir.

29. A method for supporting a human being, comprising the steps of:

providing a structure defining a configurable contoured support surface;

placing a body part of a person in contact with said support surface;

upon engagement of the body part with said support surface, periodically and automatically measuring an input parameter to determine a pressure distribution on the body part;

automatically determining a measured pressure distribution as a function of time;

automatically computing a Fourier Transform on the determined pressure distribution function and determining associated differential pressures;

storing a table of optimal comfort pressure distributions as a function of frequency and differential pressure;

automatically selecting, from the table, an optimal comfort pressure distribution based at least in part on a frequency and differential pressure computed during the step of computing; and automatically subjecting said support surface, in response to the selected optimal comfort pressure distribution, to forces tending to modify a contour of the support surface.

* * * * *